United States Patent [19]
Chao et al.

[11] Patent Number: 5,996,155
[45] Date of Patent: Dec. 7, 1999

[54] PROCESS FOR CLEANING, DISINFECTING, AND STERILIZING MATERIALS USING THE COMBINATION OF DENSE PHASE GAS AND ULTRAVIOLET RADIATION

[75] Inventors: Sidney C. Chao, Manhattan Beach; Robert W. Beach; Nelson W. Sorbo, both of Redondo Beach; Edna M. Purer, Los Angeles, all of Calif.

[73] Assignee: Raytheon Company, Lexington, Mass.

[21] Appl. No.: 09/122,390

[22] Filed: Jul. 24, 1998

[51] Int. Cl.⁶ .................................................. D06F 43/00
[52] U.S. Cl. .................................. 8/158; 8/159; 68/13 R; 68/18 R
[58] Field of Search .............................. 134/1, 1.3, 2, 10, 134/12, 40, 902; 8/158, 159, 137, 142; 68/18 R, 13 R; 210/634, 774, 805, 806

[56] References Cited

U.S. PATENT DOCUMENTS

| | | | |
|---|---|---|---|
| 4,012,194 | 3/1977 | Maffel | 8/142 |
| 4,990,260 | 2/1991 | Pisani | 210/664 |
| 5,013,366 | 5/1991 | Jackson et al. | 134/1 |
| 5,068,040 | 11/1991 | Jackson | 210/748 |
| 5,196,134 | 3/1993 | Jackson | 252/103 |
| 5,213,619 | 5/1993 | Jackson | 134/1 |
| 5,215,592 | 6/1993 | Jackson | 134/1 |
| 5,236,602 | 8/1993 | Jackson | 210/748 |
| 5,267,455 | 12/1993 | Dewees et al. | 68/5 C |
| 5,316,591 | 5/1994 | Chao et al. | 134/34 |
| 5,339,844 | 8/1994 | Stanford, Jr. et al. | 134/107 |
| 5,344,493 | 9/1994 | Jackson | 134/1 |
| 5,370,740 | 12/1994 | Chao et al. | 134/1 |
| 5,456,759 | 10/1995 | Stanford, Jr. et al. | 134/1 |
| 5,467,492 | 11/1995 | Chao et al. | 8/159 |
| 5,651,276 | 7/1997 | Purer et al. | 658/5 C |

OTHER PUBLICATIONS

James R. MacNeal et al, "Comparison Of Health Care–Based Sterilization Technologies: Safety, Efficacy, And Economics", *Journal of Healthcare Safety, Compliance & Infection Control*, vol. 1, No. 2, Dec. pp. 91–107 (1997).

*Primary Examiner*—Philip R. Coe
*Attorney, Agent, or Firm*—Colin M. Raufer; Leonard A. Alkov; Glenn H. Lenzen, Jr.

[57] ABSTRACT

A process is provided for cleaning, disinfecting, and sterilizing substrates comprising the steps of: (a) placing the contaminated substrate in a cleaning vessel; (b) contacting the contaminated substrate with dense phase carbon dioxide in liquid form; (c) subjecting the substrate and the dense phase carbon dioxide to ultraviolet radiation having a wavelength within the range of about 180 to 300 nm for a duration and intensity sufficient to produce a photochemical reaction capable of destroying the DNA of microorganisms on the substrate; (d) substantially simultaneously subjecting at least the dense phase carbon dioxide to agitation; and (e) removing the dense phase carbon dioxide from the cleaning vessel and thereby transporting the contaminants from the substrate such that the substrate is cleaned and, in the case of contaminated garments, disinfected or, in the case of medical and dental instrumentation, sterilized. Substantially simultaneously with the UV exposure and agitation, the substrates are also subjected to an oxidizing sterilant, such as $H_2O_2$.

8 Claims, 2 Drawing Sheets

PROCESS FOR CLEANING, DISINFECTING, AND STERILIZING MATERIALS USING THE COMBINATION OF DENSE PHASE GAS AND ULTRAVIOLET RADIATION

BACKGROUND OF THE INVENTION

1. Field of the Invention

The present invention is directed to a process for cleaning, disinfecting, and sterilizing materials, and, more particularly, to a process for employing the combination of dense phase gas, ultraviolet radiation, and sterilants such as $H_2O_2$ to clean, disinfect, and sterilize materials such as fabrics and medical implements.

2. Description of Related Art (A) Medical and Dental Instruments

In the health field, medical and dental instruments that enter the blood stream or sterile tissue should be sterilized before each use. Sterilization means the use of a physical or chemical procedure to destroy all microbial life and endospores. Today, main hospital sterilizing means are (a) moist heat by steam autoclaving, (b) dry heat, and (c) ethylene oxide gas. However, many medical devices and implements cannot be subjected to heat, as it leads to degradation of the device or implement.

A variety of chemical germicides (sterilants) have been used to process reusable heat-sensitive medical devices, as they promote a high level of disinfection (virtual elimination of pathogenic microorganisms, but not all microbial forms, such as bacterial endospores). There are three levels of disinfection: (1) high (kills all organisms except high levels of bacterial spores with chemical germicides registered as sterilants by the EPA), (2) intermediate (kills mycobacteria, bacteria, and most viruses, with a chemical germicide registered as a "tuberculoside" by the EPA, and (3) low (kills some viruses and bacteria with a chemical germicide registered as a hospital disinfectant by the EPA).

In general, items that only intact skin, such as garments, headboards, blood pressure cuffs, and other medical accessories, can usually be processed by washing with a detergent or using a low level disinfectant.

In all cases, the main chemical sterilization or disinfecting technology involves the use of 12/88% ethylene oxide (ETO)/hydrochlorofluorocarbon (HCFC) mixture, hydrogen peroxide ($H_2O_2$) plasma, peracetic acid ($C_2H_2O_3$)/$H_2O_2$ plasma, and vapor phase $H_2O_2$. More recently, a 10/90% ETO/$CO_2$ gas mixture has been used, where the $CO_2$ is a more environmentally "friendly" diluant for the active sterilizing species than the HCFC in the 12/88% ETO/HCFC mixture.

The most efficient of the sterilizing technologies cited are the 12/88% ETO/HCFC and 10/90% ETO/$CO_2$, as they are conducted at positive operating pressures (10 to 12 psig and 50 to 80 psig, respectively). The other known processes are conducted at sub-atmospheric pressures. The sterilization efficacy of positive pressures against challenge barriers is quoted at 97% on surfaces, but only 44% in the lumen for the 12/88% ETO/HFCF. The other sub-atmospheric technologies cited range lower still, between 32 to 78% on surfaces and 6 to 35% in the lumen. See, MacNeal et al., "Comparison of Health Care-Based Sterilization Technologies: Safety, Efficacy, and Economics", *Journal of Healthcare Safety, Compliance & Infection Control*, vol. 1, No. 2 (December 1997). Across the board, the substantially lower sterilization efficacy cited for hard to access surfaces such as that of a lumen, is due to the difficulty in cleaning biological debris from cavities prior to sterilization or to the presence of inherently higher levels of bioburden in these cavities. Though the positive pressure in the current systems does not ensure a high level of "kill" in cavities, it is better in overcoming the penetration obstacles to the sterilants in cavities, or in the face of heavy bioburden or biomass.

In addition to the above, the chemical sterilants are highly toxic, and even minor residual levels in the sterilizer, or on sterilized surfaces, can act as irritants to operators or patients.

In summary, the current challenges of chemical sterilization for medical and dental devices is related mostly to difficult to access surfaces such as that of a lumen for the rigorous pre-cleaning required for bioburden reduction, delivery of adequate levels of active sterilant for these "challenged" surfaces throughout the sterilization cycle, ability of rapidly delivering sterilants to these surfaces in order to reduce cycle time, and ability to then deactivate or efficiently separate out the residual sterilizing species to minimize the risk to the operator or patient.

(B) Garments

In the field of commercial garment cleaning/dry-cleaning, typically, garments from multiple customers are co-processed in the same machine-cleaning cycle, posing the risk of some forms of pathogen transmission through garment cross-contamination. Fluids used in conventional garment dry-cleaning do not have disinfecting properties, and disinfection in commercial dry-cleaning is not addressed.

The challenge to the commercial garment cleaning/dry-cleaning is to effect the pathogen destruction within the short agitation steps within the cleaning cycle (typically less than 10 minutes) without leading to the degradation of the fabrics themselves and without producing toxic waste.

(C) Dense Phase Carbon Dioxide; UV Radiation

Dense phase carbon dioxide is an inexpensive and virtually unlimited natural resource that is non-toxic, non-flammable, and non-smog producing. Dense phase carbon dioxide is compressed to either supercritical or subcritical conditions to achieve liquid-like densities, and is often simply termed "liquid carbon dioxide". Liquid carbon dioxide exhibits solvating properties typical of hydrocarbon solvents. Its properties make it a good organic solvent-like cleaning medium in general, and specifically, a good dry-cleaning medium for fabrics and garments.

U.S. Pat. No. 5,316,591, issued to Chao et al. and assigned to Hughes Aircraft Company, addresses part cleaning by cavitation in liquified gases. U.S. Pat. No. 5,370,740, issued to Chao et al. and assigned to Hughes Aircraft Company, addresses chemical decomposition of organic materials by sonication in liquid carbon dioxide. U.S. Pat. No. 5,013,366, issued to Jackson et al. and assigned to Hughes Aircraft Company, addresses a part cleaning process using phase shifting of dense phase carbon dioxide with or without the aid of UV, sonication, and chemical oxidants. U.S. Pat. No. 5,236,602, issued to Jackson and assigned to Hughes Aircraft Company, addresses a dense phase fluid photochemical process for liquid substrate treatment using UV, with or without chemical oxidants to chemically alter toxic materials into non-toxic species. U.S. Pat. Nos. 5,068,040 and 5,215,592, both issued to Jackson and assigned to Hughes Aircraft Company, address a dense fluid photochemical process for solid substrate treatment using UV, with or without chemical oxidants. U.S. Pat. No. 5,213,619, issued to Jackson et al., addresses a process for cleaning, sterilizing, and implanting materials using high energy (acoustic radiation or non-uniform electrostatic field) dense fluids.

Although each of the foregoing patents addresses cleaning in dense phase carbon dioxide in general, and specifically, organic chemical destruction with the aid of UV, with or without chemical oxidants, the disinfection or sterilization in dense phase carbon dioxide by UV radiation with or without chemical oxidants is not addressed. Furthermore, although U.S. Pat. No. 5,213,619 addresses a process for cleaning, sterilizing, and implanting materials using dense fluids that are energized by a non-uniform electrostatic field and high powered acoustic radiation, costly sterilizing equipment is needed, and more importantly, removal of soil from substrates is not effective.

The initial patent referencing dens phase carbon dioxide as a suitable solvent for garment dry-cleaning applications is that of Maffei, U.S. Pat. No. 4,012,194. Other patents, such as U.S. Pat. No. 5,267,455, issued to Dewees and assigned on its face to The Clorox Company and U.S. Pat. No. 5,467,492, issued to Chao et al. and assigned to Hughes Aircraft Company, also reference liquid carbon dioxide as a suitable garment dry-cleaning medium. Again, these patents fail to address garment disinfection in dense phase carbon dioxide.

UV light has proven benefits in a broad range of applications, including the disinfection of solid surfaces, liquids, air, and photochemical processes. The advantage of using UV light for disinfection lies in the fact that it controls pathogens without the use of harmful chemicals. For example, UV germicidal energy has been used to purify water. UV energy between 180 and 300 nm disrupts the DNA strands of micro-organisms and prevents cell replication. A microbe that cannot replicate dies. Microbes are particularly vulnerable to the effects of light at a wavelength at or near 253 to 254 nm, due to the resonance of this wavelength with molecular structures. This resonance breaks organic molecular bonds which in turn translate to cellular or genetic damage for microorganisms.

A major disadvantage of this photochemical destruction is that the targeted area must be in the line of sight of the radiation, in order for sterilization to occur and is thus by itself ineffective for all but relatively clean and directly irradiated targets. Addition of oxidizing species that can be readily photo-dissociated upon exposure to the UV radiation into more active species increases the efficacy of the UV sterilization, but it does not resolve the challenge of cleaning hard to access cavities and holes, such as that of a lumen, or the challenge of efficiently delivering the sterilants into these holes.

It is desirable to provide a single-step dense gas cleaning process that, in addition to cleaning a substrate, also achieves the disinfection and sterilization of substrates using simple, faster, economical, and less toxic techniques. The present invention fulfills these needs.

SUMMARY OF THE INVENTION

A new and improved process for cleaning, disinfecting, and sterilizing substrates is provided herein which possess substantially all of the advantages of the above-described systems while overcoming most of their significant disadvantages. More specifically, in accordance with the invention, a process is provided for removing contaminants from a preselected substrate, with the targeted contaminants including soiling substances as well as microorganisms. The process comprises the following steps:

(a) placing the contaminated substrate in a cleaning vessel;

(b) contacting the contaminated substrate with liquid carbon dioxide;

(c) subjecting the substrate and the liquid carbon dioxide to ultraviolet radiation having a wavelength within the range of about 180 to 300 nm for a duration and intensity sufficient to produce a photochemical reaction capable of breaking the organic molecular bonds within the microorganisms, thereby destroying their DNA and resulting in fragmented biological contaminants;

(d) subjecting the substrate and the liquid carbon dioxide substantially simultaneously to agitation; and (e) removing the liquid carbon dioxide from the cleaning and disinfection vessel and thereby transporting the contaminants, including the fragmented biological contaminants, from the substrate such that the substrate is cleaned, disinfected and/or sterilized.

Thus, in accordance with the invention, the substrate to be cleaned is exposed in a single process vessel to liquid carbon dioxide (dense phase carbon dioxide) as well as to ultraviolet (UV) radiation and agitation in order to achieve both a clean surface rid of soiling substances as well as a disinfected surface substantially free from microorganisms. In this manner, substrates may be inexpensively cleaned and disinfected, and even sterilized, in an environmentally-friendly but still highly effective and efficient manner.

In particular, in one embodiment, the present invention is directed to a process where UV light, with or without the presence of sterilants such as, but not limited to, $H_2O_2$, is used to disinfect or sanitize commercial garments processed in a liquid carbon dioxide garment dry-cleaning process, that uses high velocity jets as a means of mechanical agitation.

Further, in a second embodiment, the present invention is directed to a process that uses dense phase carbon dioxide under vigorous agitation produced by cavitation shear and convection with sonic whistles or cavitational blades, in conjunction with UV light and chemical oxidants such as, but not limited to, $H_2O_2$ to accomplish surface pre-cleaning, sterilization, and then residual sterilant destruction within a single process of cleaning and sterilizing medical or dental devices. Specifically, this embodiment emphasizes cavitation for removal of soil from surfaces and transport away from the surfaces, with sterilant transport to those surfaces shaded from direct UV exposure.

These and many other features and attendant advantages of the present invention will become apparent as the invention becomes better understood by reference to the following detailed description when considered in conjunction with the accompanying drawings.

DETAILED DESCRIPTION OF THE PREFERRED EMBODIMENTS

Figure 1:
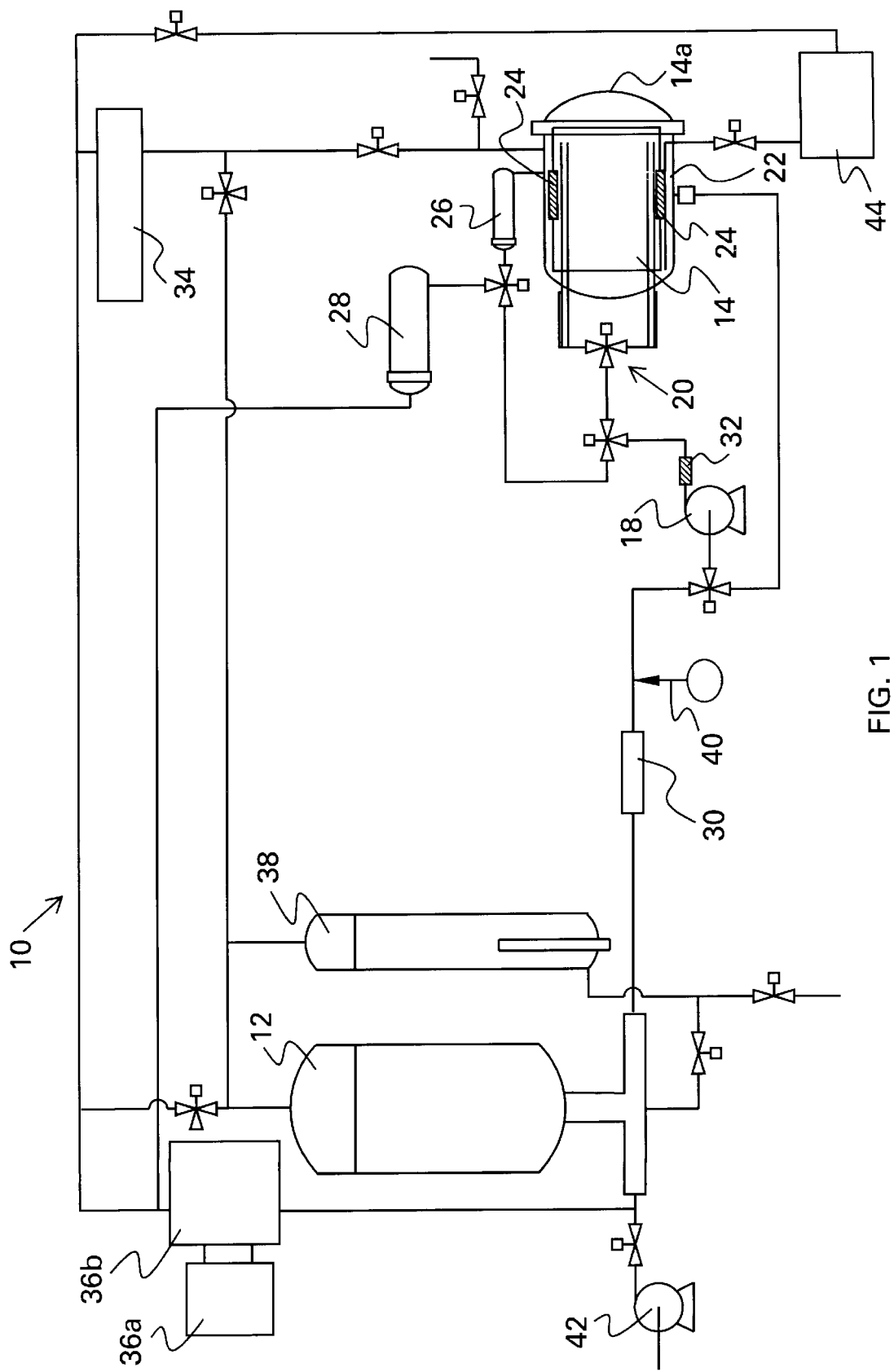
FIG. 1 is a schematic representation of a system for practicing a preferred exemplary process of the present invention in which garments may be dry-cleaned and disinfected with treatments by both dense phase carbon dioxide and UV radiation.

The present invention is directed to a new and improved process for cleaning, disinfecting, and sterilizing substrates. Essentially, the process employs ultraviolet radiation in conjunction with sterilants such as, but not limited to, $H_2O_2$ to destroy pathogens on the substrate, as well as to fragment organic bonds within organic soiling materials, and employs dense phase gas in liquid form to transport pathogen and organic fragments as well as other inorganic soiling materials from the substrate. Vigorous agitation is employed in conjunction with the UV irradiation and $H_2O_2$ to enhance the efficacy of the process. The combination of vigorous agitation, UV irradiation, and sterilant is essential to the soil removal from "challenged" surfaces and to the fast transport of the sterilant to these surfaces. As used herein, the term "challenged surface" refers to a surface that is relatively inaccessible to fluid, UV radiation, and agitation. Thus, the present invention represents a new and nonobvious combination of two known techniques to clean, disinfect, and sterilize substrates in an economical, efficient, and environmentally-friendly manner.

The dense phase fluid which is used in accordance with the present invention comprises carbon dioxide which may be converted to a supercritical fluid or liquefied at temperatures and pressures which will not degrade the physical or chemical properties of the substrate being cleaned.

Dense phase carbon dioxide is compatible with all substrates contemplated for cleaning, and has a low cost and high health and safety ratings. Further, dense phase carbon dioxide is non-flammable and environmentally-friendly. Also, dense phase carbon dioxide does not dissociate when exposed to the selected radiation used in the present process, or if it does dissociate, it forms products which are useful and desired in the present process.

Carbon dioxide is an easily liquefiable natural resource. Once liquefied, it offers a good, low viscosity medium at relatively low pressure (about 600 to 1,040 psi or about 42.2 to 73.1 $kg/cm^2$) and mild temperatures (about 10° to 30° C.). These values are below the critical pressure of 1071 psi (75.3 $kg/cm^2$) and the critical temperature 32° C. for carbon dioxide. The dense (or compressed) gas phase above the critical temperature and near or above the critical pressure is often referred to as a "supercritical fluid".

The radiation used in practicing the present process is selected to produce the dissociation of the undesired material or contaminant, and more particularly the dissociation of organic bonds within soiling substances and biological contaminants. The preferred radiation comprises ultraviolet (UV) radiation within the range of about 180 to 300 nm, which disrupts the DNA strands of microorganisms and prevents cell replication. In particular, it is known that microbes are uniquely vulnerable to the effect of light at wavelengths at or near 253 to 254 nm due to the resonance of this wavelength with molecular structures and the resulting molecular bond breakage that occurs upon exposure. Ultraviolet radiation may be produced in any commercially available manner, such as mercury arc lamps or xenon flash lamps. Operation of such lamps may be continuous or high energy burst pulsed, so long as the latter is suitable for cleaving contaminant bonds.

It is noted that, in addition to destroying pathogens, the radiation may also alter the molecular structure and properties of the dense fluid so as to enhance its cleaning ability, as recognized by Jackson (U.S. Pat. Nos. 5,068,040 and 5,236,602, both described above). The enhanced cleaning ability of the dense phase fluid exposed to UV radiation derives from the believed polarity of the dense phase fluid induced by photoexcitation.

There are a number of techniques to improve the effectiveness of the ultraviolet radiation in photodissociating organic molecular bonds. One technique involves increasing the internal reflection of the chamber by including a radiation-reflecting liner on its interior surface. By scattering the radiation throughout the cleaning vessel by introducing additional internal reflection, there is greater exposure of the substrate surfaces to the radiation. This phenomena decreases the dependence of substrate distance from the radiation source for effective surface cleaning.

More specifically, adding an oxidizing sterilant, e.g., $H_2O_2$ that will dissociate into more active radicals when irradiated by UV, coupled with vigorous fluid agitation, such as with a cavitating blade or sonic whistle, will transport these active species into holes and crevices that are shaded from direct exposure to the UV. Thus, on UV-shaded, challenged access surfaces, pathogen obstruction occurs through sterilant exposure (as activated by UV and delivered by agitation).

Therefore, the ultraviolet radiation employed in the practice of the invention directly destroys pathogens associated with the substrate and indirectly activates sterilants that effect sterilization, and thereby enhances the cleaning ability of the dense phase fluid by photoexcitation. Additionally, the photolysis of the present invention achieves a size reduction in larger organic and inorganic molecules, which are cleaved into smaller fragments that are easier to solvate or suspend in the dense phase fluid than larger molecules. Therefore, in addition to destroying pathogens and photoexciting the dense phase fluid, the photolysis of the present invention decreases surface cleaning time by increasing soil solvation and suspension in dense fluids.

The dense phase fluid also serves multiple purposes when combined with ultraviolet radiation exposure, such as serving as an effective radiation transmission medium, a cleaning solvent, and waste carrier. The agitated dense phase fluid bathes the substrate surface and dissolves or suspends the soils, including biological contaminants, which are photolytically or chemically (when sterilants are present) dissociated and accordingly destroyed. The dense phase fluid then suspends and transports the decomposition products as well as other soils dissolved or dislodged by agitation, rendering surfaces both clean and sterile.

Thus, the present process simultaneously provides both the cleaning step and the disinfection and sterilization steps that have been performed in separate steps in prior art processes discussed above. The dense phase fluid under vigorous agitation and the UV radiation and sterilants such as $H_2O_2$ work together to achieve both cleanliness and disinfection and/or sterilization of substrates.

The process of the present invention may be used to clean, disinfect, and sterilize a wide variety of substrates formed of a variety of materials. Typical substrates from which soils may be removed by the present process include, but are not limited to, substrates formed of metals, fabrics, cellulose, rubbers, ceramics, carbon, glasses, polymeric materials, and other organic or inorganic compounds. In addition, the substrate may be in the form of particulate matter or other finely divided material. The substrate may also comprise water or other liquid carrier for waste materials. The process is especially well adapted and contemplated for cleaning and disinfecting/sterilizing garments and other fabrics as well as medical and dental instrumentation.

Inorganic and organic soils can be removed simultaneously in accordance with the present process. Organic soils absorb UV radiation causing bond cleavage, while inorganic materials are removed through solvation or fluidation in the dense phase media.

In a first embodiment of the present invention, the undesired material which is removed comprises a contaminant, such as a hydrocarbon material or biological material, on the surface of substrate, such as garments and fabrics or medical and dental implements. In another related embodiment, the undesired material which is removed and destroyed comprises pathogens or dissolved organic soils, suspended in the liquid $CO_2$ medium.

Turning now to the drawings, wherein like reference numerals designate like elements, an exemplary cleaning and disinfection system for practicing the present invention is shown diagrammatically in FIG. 1. Specifically, the system 10 depicted in FIG. 1 is a dense phase gas garment dry-cleaning system 10 that employs ultraviolet radiation to achieve disinfection of the garments and recirculating fluid. The various parts of the apparatus are conventional and have been disclosed elsewhere. Although specific details of the apparatus are not described here, it is believed that those skilled in the art can use the teachings of the present invention to construct suitable apparatus to carry out the process of the present invention.

As shown in FIG. 1, the exemplary cleaning and sterilization system for use in practicing the present invention includes a gas supply, with the dense gas being formed by known methods of controlling temperature and pressure. The liquid dense phase gas is stored in a storage vessel 12 at approximately 915 psi and 25° C., for example. The storage vessel 12 is conventional, and comprises any material capable of containing the dense phase gas at required high pressures.

FIG. 1 depicts a cleaning chamber 14 equipped with lid 14a suitably employed in the practice of the invention. Garments are placed in a perforated cleaning basket 16 within the cleaning chamber 14, the lid 14a is closed, and the chamber is pressurized. Liquid carbon dioxide is introduced into the chamber 14 from the storage vessel 12 by a pump 18, via a set of high velocity fluid jet manifolds 20, and the reversible agitation of the garment load is commenced, as described in U.S. Pat. No. 5,467,492, supra. As the garments accelerate, and span the peripheral cleaning zone of the perforated cleaning basket 16, the soil is expelled from the garments and from the basket into the zone 22 between the basket wall and the cleaning chamber wall and then out of the cleaning chamber 14. During this agitation step, the garments are exposed to UV radiation from a UV radiation source 24, such as a mercury lamp, of an appropriate intensity to cause sterilization/disinfection, at one or more peripheral basket areas. The fluid is re-circulated in a closed loop through a lint trap 26 and a batch of filters 28 which serve to remove insoluble particulates. The re-circulating fluid can also be exposed to the UV light at optional points, such as denoted at 30, within the re-circulating loop, preferably before the pump inlet from the pump 18. The UV exposure can take place alone or in conjunction with chemical oxidizing agents such as hydrogen peroxide, injected into the re-circulating loop in a manner that promotes its dispersion by the recirculating liquid carbon dioxide, i.e., at the pump discharge 32. At the end of the cleaning/agitation/disinfection step, the fluid is drained back into the storage vessel 12. The gaseous $CO_2$ is recovered back into the storage vessel 12 via a compressor 34 and re-condensed into liquid by a refrigerator 36a/condensor 36b.

Other elements of the system 10 include a still 38, which is used to distill solubilized soils or spent sterilant, a pump 42 that replenishes the storage tank 12 with fresh liquid $CO_2$, and a sterilant pump 40 typically positioned at or near the main pump 18 inlet to promote the dispersion of the sterilant into the main liquid $CO_2$ medium. In addition, a heater 44 may be used to heat the $CO_2$, if desired.

In garment dry-cleaning/disinfection, typical process temperatures (in the cleaning chamber 14) are below 32° C., with pressure below the critical pressure of 1071 psi.

The typical exposure time of the articles to be cleaned will vary, depending upon the nature of the substrate being cleaned, the degree of soiling, and so forth. However, when working with fabrics, a typical exposure time to the dense phase gas is between about 5 to 10 minutes, while the typical exposure time to the ultraviolet radiation is within the range of about 5 to 10 minutes. However, some substrates, such as hospital garments, may require somewhat longer agitation and UV exposure.

The liquid suspension medium, i.e., the dense phase fluid within the chamber 14, may contain additives, such as dense phase gas oxidants, which enhance the cleaning process. The oxidants may be photodissociated by the UV radiation, with the result that the photodissociated species have increased reactivity with the soils and pathogens and enhance their removal or destruction. Examples of additives that may be employed include an oxidizing gas, such as ozone, and oxidants, such as hydrogen peroxide. However, the invention is not limited to these specific additives.

Hydrogen peroxide is the preferred reactive agent for use in the present process and is preferably employed in the dry-cleaning garment system depicted in FIG. 1. Hydrogen peroxide can be photodissociated to hydroxyl radicals and peroxide radicals, which react with soils and form innocuous carbon dioxide and water by-products. Thus, hydrogen peroxide enhances the cleaning qualities of dense phase carbon dioxide without adding toxicity to the process and offers the added advantage of serving as a biocide. Additionally, unlike carbon dioxide, hydrogen peroxide has a large dipole and low dielectric strength. Accordingly, a mixture of carbon dioxide and hydrogen peroxide in varying ratios may possess a wide range of hydrogen bonding, polar, and dipole energy contributions, hence may offer a wide variety of solubility chemistries.

Figure 2:
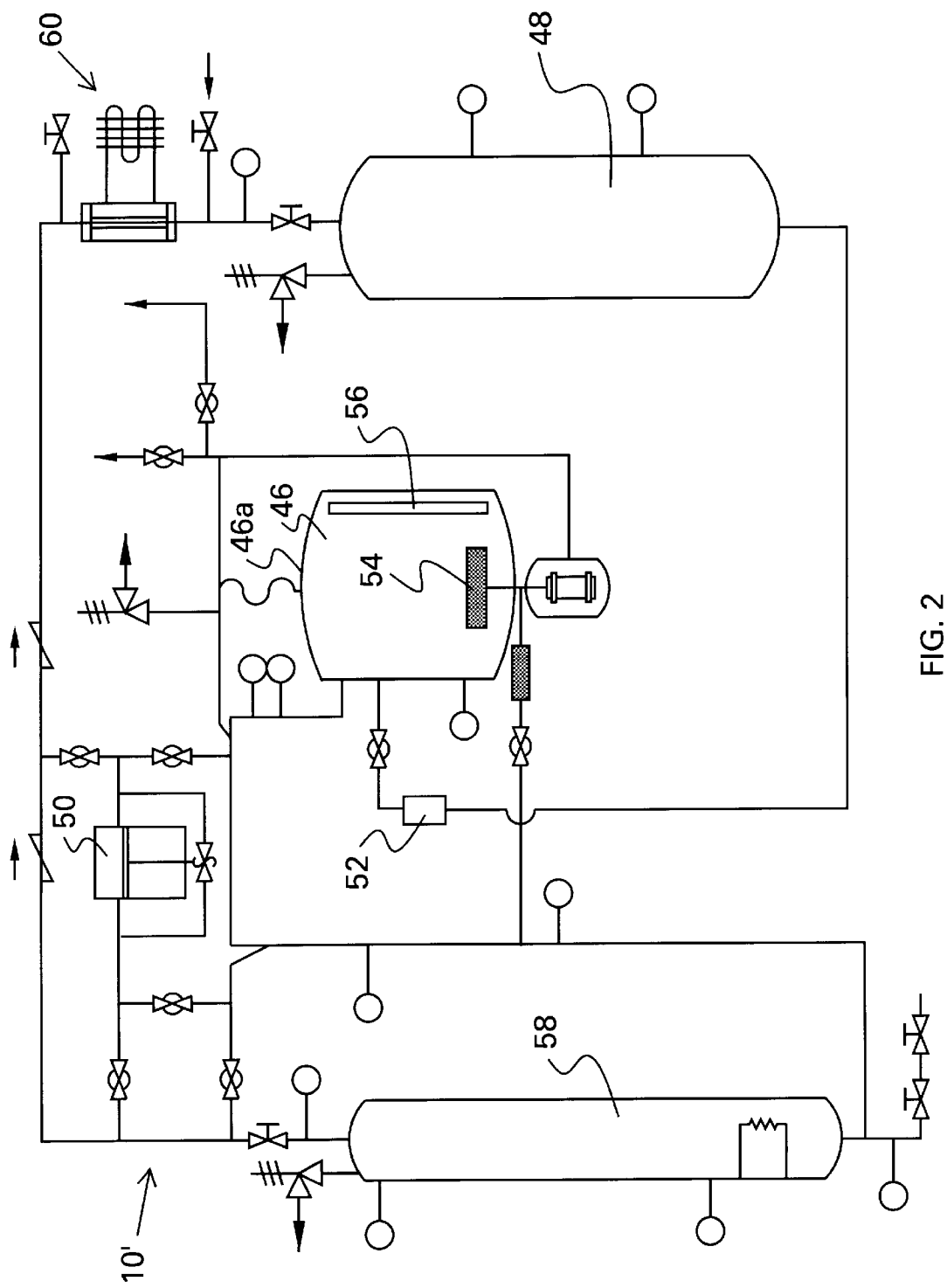
FIG. 2 is a schematic representation of a system for practicing a preferred exemplary process of the present invention in which medical and/or dental instrumentation may be cleaned and sterilized with treatments by both dense phase carbon dioxide and UV radiation.

Turning now to FIG. 2, a part cleaning, disinfection, and sterilization system 10' in accordance with the present invention is depicted therein, with the parts specifically being contemplated to be medical and dental instrumentation. In this embodiment, the parts themselves are typically stationary, to prevent damage to the parts, and since vigorous agitation is employed, typically part fixturing or traying (not shown) is required. The vigorous agitation necessary for cleaning and even transport and distribution of chemical oxidants needed for sterilization/disinfection is provided by vigorous shear cavitation, such as generated by ultrasonic transducers, horns, cavitation blades, or sonic whistles. The use of shear cavitation in conjunction with dense phase gas cleaning is disclosed elsewhere; see, e.g., U.S. Pat. No. 5,316,591, supra. FIG. 2 represents an exemplary dense phase carbon dioxide part cleaning system that also embodies the part disinfection/sterilization process of the present invention, using cavitation, UV irradiation of parts, and fluid and chemical oxidants.

A typical dense phase carbon dioxide part cleaning and disinfection process is as follows: the parts are placed in the cleaning chamber 46 and the lid 46a is closed and the chamber is pressurized. Liquid carbon dioxide is introduced into the chamber 46 from a storage tank 48 by a compressor 50. A chemical oxidant (such as, but not limited to hydrogen peroxide or ozone) preferentially located at the fluid inlet path 52 is introduced into the chamber 46 along with the liquid carbon dioxide medium. A cavitation disk 54 is employed in the chamber 46, and the disk 54 is activated along with the ultraviolet radiation source 56, which in the system 10' depicted in FIG. 2 is contained within the chamber 46 itself, thereby promoting the illumination of the exposed parts.

Agitation via the cavitation disk 54 is continued for a predetermined amount of time, typically for a period of time within the range of about 5 to 10 minutes. The cleaning fluid is thereafter drained from the chamber 46 to a still 58 and distilled back to storage 46 and recondensed to a liquid state by the refrigeration/condenser 60. The time period of cavitation is essentially the time period is same as UV exposure, which is derived from EPA guidelines, as referenced in EPA Design Manual for Municipal Waste Water Disinfection.

Typical process temperatures for carbon dioxide are below the critical temperature of 32° C. and the typical process pressure is below 1071 psi, such that the cleaning medium is in a liquid form.

The necessary processing parameters, i.e., gas type and gas mixture ratios, temperatures, and pressures necessary to achieve the desired cleanliness and sterility levels, are dependent upon the nature and extent of contamination and the configuration of the material being processed. An estimation of such parameters may be made using the EPA guidelines presented in the above-referenced EPA Design Manual, using the UV Density Method employed.

The cleaning vessels 14, 46 shown in FIGS. 1 and 2, respectively, are exemplary only, and other possible cleaning vessel configurations may be used in order to carry out the process of the present invention. For example, a wide variety of external and internal heating and cooling elements may be utilized in order to provide the necessary temperature control to accomplish phase shifting of the dense fluid between the liquid and supercritical fluid states, if such phase shifting is employed. Also, cleaning vessels may be used wherein several types of cavitation-producing agitation methods are incorporated into the cleaning chamber 14, 46 along with the ultraviolet radiation features.

Thus, there has been disclosed an improved process for cleaning, disinfecting, and sterilizing substrates. It will be readily apparent to those of ordinary skill in this art that various changes and modifications of an obvious nature may be made without departing from the spirit of the invention, and all such changes and modifications are considered to fall within the scope of the invention, as defined by the appended claims.

What is claimed is:

1. A process for sterilizing fabrics and garments and removing soils therefrom, including microorganisms comprising organic molecular bonds in the form of DNA, said process comprising the steps of:
   (a) placing at least one said garment containing said soils in a cleaning and disinfecting vessel;
   (b) contacting said at least one garment containing said soils with dense phase carbon dioxide in liquid form;
   (c) subjecting said at least one garment and said dense phase carbon dioxide to ultraviolet radiation having a wavelength within the range of about 180 to 300 nm for a duration and intensity sufficient to produce a photochemical reaction that breaks said organic molecular bonds, thereby destroying said DNA and resulting in fragmented biological contaminants;
   (d) substantially simultaneously subjecting said at least one garment to mechanical agitation; and
   (e) removing said dense phase carbon dioxide from said cleaning and disinfection vessel and thereby transporting said soils, including said fragmented biological contaminants, from each said garment such that each said garment is cleaned and disinfected.

2. The process of claim 1 wherein said mechanical agitation is performed by a set of fluid jet manifolds to mechanically agitate said garment and said dense phase carbon dioxide.

3. The process of claim 1 wherein said radiation has a wavelength within the range of about 253 to 254 nm.

4. The process of claim 1 wherein step (b) further comprises contacting said at least one garment with a sterilizing agent to enhance destruction of said microorganisms.

5. The process of claim 4 wherein said sterilizing agent is an oxidizing agent selected from the group consisting of an oxygen-containing compound and a hydrogen-containing compound.

6. The process of claim 5 wherein said sterilizing agent is selected from the group consisting of hydrogen peroxide and ozone.

7. The process of claim 6 wherein said hydrogen peroxide is mixed with said dense phase gas prior to introduction into said cleaning and disinfecting vessel.

8. The process of claim 1 wherein said biological contaminant is selected from a group consisting of bacteria and spores.

* * * * *